United States Patent
Ju et al.

(10) Patent No.: US 9,990,765 B2
(45) Date of Patent: Jun. 5, 2018

(54) APPARATUS AND METHOD FOR GENERATING PRINTING DATA FOR PATIENT-SPECIFIC APPLICATOR, AND SYSTEM FOR MANUFACTURING PATIENT-SPECIFIC APPLICATOR

(71) Applicant: Samsung Life Public Welfare Foundation, Seoul (KR)

(72) Inventors: Sang Gyu Ju, Seoul (KR); Won Park, Gyeonggi-do (KR); Doo Ho Choi, Seoul (KR); Youngyih Han, Seoul (KR); Yong Chan Ahn, Seoul (KR); Seung Jae Huh, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 315 days.

(21) Appl. No.: 14/890,850

(22) PCT Filed: Apr. 25, 2014

(86) PCT No.: PCT/KR2014/003638
§ 371 (c)(1),
(2) Date: Nov. 12, 2015

(87) PCT Pub. No.: WO2014/185637
PCT Pub. Date: Nov. 20, 2014

(65) Prior Publication Data
US 2016/0093100 A1    Mar. 31, 2016

(30) Foreign Application Priority Data

May 15, 2013 (KR) .................... 10-2013-0055249

(51) Int. Cl.
*G06T 17/00* (2006.01)
*G06T 19/20* (2011.01)
(Continued)

(52) U.S. Cl.
CPC ............ *G06T 17/00* (2013.01); *A61N 5/1007* (2013.01); *G05B 19/4099* (2013.01);
(Continued)

(58) Field of Classification Search
CPC ......... G06T 15/08; G06T 17/00; G06T 19/20; G06T 2200/08; G06T 2210/41;
(Continued)

(56) References Cited

U.S. PATENT DOCUMENTS

| 2010/0194750 | A1* | 8/2010 | Mielekamp ............. G06T 19/00 345/424 |
| 2011/0052036 | A1* | 3/2011 | Valdivieso Cacique ............... A61N 5/1031 382/132 |

(Continued)

FOREIGN PATENT DOCUMENTS

| JP | 2011-516231 A | 5/2011 |
| KR | 10-2011-0035214 A | 4/2011 |
| KR | 10-2012-0088928 A | 8/2012 |

OTHER PUBLICATIONS

International Search Report, prepared by KIPO as the ISA, for international application PCT/KR2014/003638 dated Aug. 20, 2014.

(Continued)

*Primary Examiner* — Shahed Ahmed
(74) *Attorney, Agent, or Firm* — McCarter & English, LLP (57) ABSTRACT

A system for manufacturing a patient-specific applicator reconstructs a three-dimensional (3D) image by using a medical image of a patient, models an applicator structure for irradiating radiation onto a tumor tissue, based on a 3D image, generates printing data for 3D printing for manufacturing the patient-specific applicator based on the modeled (Continued)

applicator structure, and manufactures the patient-specific applicator based on the generated printing data.

14 Claims, 5 Drawing Sheets (51) Int. Cl.
    *A61N 5/10*     (2006.01)
    *G05B 19/4099*     (2006.01)
    *G06T 11/00*     (2006.01)
    *G06T 15/08*     (2011.01)
    *B33Y 50/02*     (2015.01)
    *B33Y 80/00*     (2015.01)
    *A61B 34/10*     (2016.01)

(52) U.S. Cl.
CPC .......... *G06T 11/003* (2013.01); *G06T 11/008* (2013.01); *G06T 15/08* (2013.01); *G06T 19/20* (2013.01); *A61B 2034/105* (2016.02); *A61B 2034/108* (2016.02); *B33Y 50/02* (2014.12); *B33Y 80/00* (2014.12); *G05B 2219/35134* (2013.01); *G05B 2219/49007* (2013.01); *G06T 2200/08* (2013.01); *G06T 2210/41* (2013.01); *G06T 2219/2021* (2013.01)

(58) Field of Classification Search
CPC ........ A61B 2034/105; A61B 2034/108; B33Y 50/02; B33Y 80/00; B33Y 10/00; B33Y 30/00; B33Y 40/00; B33Y 50/00; G05B 2219/35134; G05B 2219/49007; G05B 2219/45238; G05B 19/4099; B29C 70/382; Y02P 90/265
USPC ... 700/98, 117, 119, 97, 118, 187, 103, 131, 700/262
See application file for complete search history.

(56) References Cited

U.S. PATENT DOCUMENTS

| | | |
|---|---|---|
| 2012/0191192 A1 | 7/2012 | Park et al. |
| 2015/0198943 A1* | 7/2015 | Kotlus ................. B22F 3/1055 623/17.16 |

OTHER PUBLICATIONS

Written Opinion, prepared by KIPO as the ISA, for international application PCT/KR2014/003638 dated Aug. 20, 2014.
Office action from KIPO for priority application KR 10-2013-0055249 dated Jan. 29, 2015.
Notice of Allowance from KIPO for priority application KR 10-2013-0055249 dated Oct. 13, 2015.

* cited by examiner

<MODELING OF APPLICATOR USING 3D IMAGE OF PATIENT>

APPARATUS AND METHOD FOR GENERATING PRINTING DATA FOR PATIENT-SPECIFIC APPLICATOR, AND SYSTEM FOR MANUFACTURING PATIENT-SPECIFIC APPLICATOR

CROSS-REFERENCE TO RELATED APPLICATIONS

This application is the National Stage entry under 35 U.S.C. § 371 of International Application No. PCT/KR2014/003638 filed on Apr. 25, 2014, published on Nov. 20, 2014 under publication number WO 2014/185637 A1, which claims the benefit of priority under 35 U.S.C. § 119 of Korean Patent Application Number 10-2013-0055249 filed May 15, 2013.

TECHNICAL FIELD

The present invention relates to a patient-specific applicator, and a method, an apparatus, and a system for manufacturing a patient-specific applicator, and more particularly, a patient-specific applicator manufactured by using a three-dimensional (3D) printing device, and a method, an apparatus, and a system for manufacturing a patient-specific applicator by using a 3D printing device.

BACKGROUND ART

Recently, with the increase in aging population due to an increase in average lifespan and the development of an early diagnosis technology, the number of cancer patients has tended to abruptly increase. The statistics published by the Ministry of Health, Welfare and Family Affairs in 2008 show that if people live up to an average lifespan, one out of three Koreans has cancer. A radiation treatment is one of three cancer treatment methods together with surgery and anti-cancer therapy and has gradually increased its role. An object of the radiation treatment is to necrose a tumor or suppress growth of the tumor by concentrating high dose radiation on the tumor while minimizing damage to normal surrounding organs.

Brachytherapy is a therapy that treat a cancer by irradiating high dose radiation onto a tumor while minimizing damage to normal surrounding organs by directly injecting an isotope into the center or periphery of a tumor. Since the brachytherapy can be performed alone or in combination with an external radiation treatment and can directly irradiate the high dose radiation onto the tumor, the brachytherapy is widely known as a standard radiation therapy for a cervical cancer that is a female's representative disease. The brachytherapy is one of three-dimensional conformal radiation therapy that uses the effect that very high dose is irradiated onto a region adjacent to a source of the injected isotope but the dose rapidly decreases as a distance from the source increases on the basis of an inverse square law. Therefore, for the success of the brachytherapy, it is important to effectively arrange sources in the proximity of a tumor to be treated.

DETAILED DESCRIPTION OF THE INVENTION

Technical Problem

Provided are an apparatus and a method of generating printing data for a patient-specific applicator and a system for manufacturing a patient-specific applicator. The technical problem to be solved by the present embodiment is not limited to the above-described technical problems and other technical problems may also exist.

Technical Solution

According to an aspect, an apparatus for generating printing data for a patient-specific applicator, the apparatus includes: an image reconstruction unit to reconstruct a three-dimensional (3D) image depicting an anatomical structure of a patient's body by using a medical image acquired from the patient; an applicator modeling unit to model an applicator structure based on the anatomical structure depicted in the reconstructed 3D image, the applicator structure being to be inserted into the patient's body so as to irradiate radiation onto a tumor tissue included in the acquired medical image; and a printing data generation unit to generate printing data for 3D printing for manufacturing the patient-specific applicator, based on the modeled applicator structure.

In addition, the applicator modeling unit models an internal structure of the applicator by modeling a passage of an applicator hole, into which a radiation source subjected to short-distance radiation irradiation onto the tumor tissue is inserted, based on a position of the tumor tissue appearing on the reconstructed 3D image.

In addition, the applicator modeling unit models an internal material of the applicator surrounding the applicator hole such that the short-distance radiation irradiation is performed on the tumor tissue when the radiation source is inserted into the applicator hole.

In addition, when the radiation source is inserted into the applicator hole, the applicator modeling unit partially differently models a density or a component of the internal material so as to shield short-distance radiation irradiation on normal tissues.

In addition, the applicator modeling unit models an external structure of the applicator by displaying a mark for indicating an insertion degree of the applicator in the inside of the patient's body on a surface of the applicator.

In addition, the applicator modeling unit further models a joining means that is connectable to one end of the applicator and guides a connection to an external treatment device or a fixing device.

In addition, the image reconstruction unit reconstructs a 3D density image depicting density distributions of internal constituent materials of the patient's body by using pixel values of the medical image acquired from the patient, the apparatus further includes a simulation unit to simulate a change in the patient's body, in a case where the applicator is inserted, by using a change in pixel values of positions at which the modeled applicator structure is to be inserted in the reconstructed 3D density image, and the printing data generation unit to generate the printing data when it is determined through a simulation result that there is no problems in the applicator or the patient.

According to another aspect, a method for generating printing data for a patient-specific applicator includes the steps of reconstructing a 3D image depicting an anatomical structure of a patient's body by using a medical image acquired from the patient; modeling an applicator structure based on the anatomical structure depicted in the reconstructed 3D image, the applicator structure being to be inserted into the patient's body so as to irradiate radiation onto a tumor tissue included in the acquired medical image;

and generating printing data for 3D printing for manufacturing the patient-specific applicator, based on the modeled applicator structure.

In addition, the modeling step models an internal structure of the applicator by modeling a passage of an applicator hole, into which a radiation source subjected to short-distance radiation irradiation onto the tumor tissue is inserted, based on a position of the tumor tissue appearing on the reconstructed 3D image.

In addition, the modeling step models an internal material of the applicator surrounding the applicator hole such that the short-distance radiation irradiation is performed on the tumor tissue when the radiation source is inserted into the applicator hole.

In addition, the modeling step models an external structure of the applicator by displaying a mark for indicating an insertion degree of the applicator in the inside of the patient's body on a surface of the applicator.

In addition, the method further includes the step of modeling a joining means that is connectable to one end of the modeled applicator structure and guides a connection to an external treatment device or a fixing device, wherein the generating step generates the printing data based on the modeled applicator structure and the joining means.

In addition, the method further includes the steps of reconstructing a 3D density image depicting density distributions of internal constituent materials of the patient's body by using pixel values of the medical image acquired from the patient; and simulating a change in the patient's body, in a case where the applicator is inserted, by using a change in pixel values of positions at which the modeled applicator structure is to be inserted in the reconstructed 3D density image, wherein the generating step generates the printing data when it is determined through a simulation result that there is no problems in the applicator or the patient.

According to another aspect, a system for manufacturing a patient-specific applicator includes: a computing device that reconstructs a 3D image depicting an anatomical structure of a patient's body by using a medical image acquired from the patient, models an applicator structure based on the anatomical structure depicted in the reconstructed 3D image, the applicator structure being to be inserted into the patient's body so as to irradiate radiation onto a tumor tissue included in the acquired medical image, and generates printing data for 3D printing for manufacturing the patient-specific applicator, based on the modeled applicator structure; and a 3D printing device that manufactures the patient-specific applicator based on the generated printing data.

In addition, the computing device models an internal structure of the applicator by modeling a passage of an applicator hole, into which a radiation source subjected to short-distance radiation irradiation onto the tumor tissue is inserted, based on a position of the tumor tissue appearing on the reconstructed 3D image.

In addition, the computing device models an internal material of the applicator surrounding the applicator hole such that the short-distance radiation irradiation is performed on the tumor tissue when the radiation source is inserted into the applicator hole.

Advantageous Effects of the Invention

According to the above description, it is possible to design the patient-specific applicator by using the 3D image having the same condition as the anatomical structure of the patient and manufacture the designed patient-specific applicator by using the 3D printing device. Therefore, it is possible to perform an optimized brachytherapy on a tumor tissue according to an actual body type of a patient. That is, the patient-specific applicator manufactured by using the 3D printing device can perform brachytherapy more accurately than the stereotyped or uniform type of an applicator. In addition, since the 3D printing device is used, the applicator suitable for the patient's actual body type can be manufactured more easily and at a low cost.

BEST MODE

An apparatus for generating printing data for a patient-specific applicator, the apparatus includes: an image reconstruction unit that reconstructs a three-dimensional (3D) image depicting an anatomical structure of a patient's body by using a medical image acquired from the patient; an applicator modeling unit that models an applicator structure based on the anatomical structure depicted in the reconstructed 3D image, the applicator structure being to be inserted into the patient's body so as to irradiate radiation onto a tumor tissue included in the acquired medical image; and a printing data generation unit that generates printing data for 3D printing for manufacturing the patient-specific applicator, based on the modeled applicator structure.

A method for generating printing data for a patient-specific applicator includes the steps of reconstructing a 3D image depicting an anatomical structure of a patient's body by using a medical image acquired from the patient; modeling an applicator structure based on the anatomical structure depicted in the reconstructed 3D image, the applicator structure being to be inserted into the patient's body so as to irradiate radiation onto a tumor tissue included in the acquired medical image; and generating printing data for 3D printing for manufacturing the patient-specific applicator, based on the modeled applicator structure.

A system for manufacturing a patient-specific applicator includes: a computing device that reconstructs a 3D image depicting an anatomical structure of a patient's body by using a medical image acquired from the patient, models an applicator structure based on the anatomical structure depicted in the reconstructed 3D image, the applicator structure being to be inserted into the patient's body so as to irradiate radiation onto a tumor tissue included in the acquired medical image, and generates printing data for 3D printing for manufacturing the patient-specific applicator, based on the modeled applicator structure; and a 3D printing device that manufactures the patient-specific applicator based on the generated printing data.

MODE OF THE INVENTION

Hereinafter, embodiments of the present invention will be described. The following deceptions and the accompanying drawings are provided for understanding operations according to the present embodiment, and portions that can be easily carried out by those skilled in the art may be omitted.

In addition, the present specification and the drawings are not intended to limit the present embodiment, and the scope of the present embodiment should be defined by the following claims. It should be understood, however, that this is not intended to limit the present embodiment to a particular form disclosed herein, but rather, this covers all modifications, equivalents, and alternatives falling within the spirit and scope of the present embodiment.

Hereinafter, the present embodiment will be described in more detail with reference to the accompanying drawings.

Figure 1:
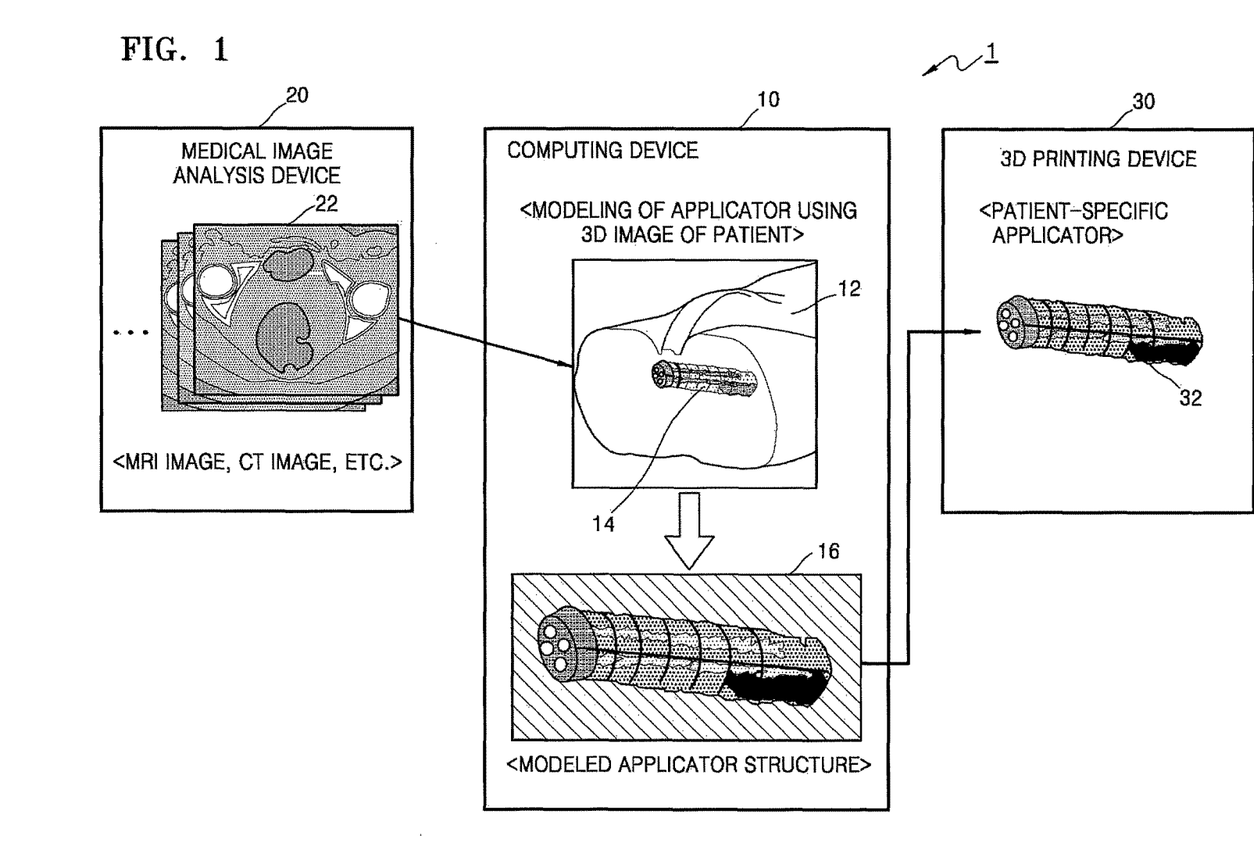
FIG. 1 is a diagram illustrating a system for manufacturing a patient-specific applicator, according to an embodiment of the present invention.

FIG. 1 is a diagram illustrating a system 1 for manufacturing a patient-specific applicator 32, according to an embodiment of the present invention. Referring to FIG. 1, the system 1 for manufacturing the patient-specific applicator 32 includes a computing device 10, a medical image analysis device 20, and a 3D printing device 30.

The system 1 for manufacturing the patient-specific applicator 32, according to the present embodiment, is a system for manufacturing an applicator that is inserted into a patient's body to treat a tumor tissue by irradiating proximity radiation in the proximity of the tumor tissue for the purpose of a medical procedure of brachytherapy.

A radiation treatment is one of three cancer treatment methods together with surgery and anticancer therapy and has gradually increased its role. An object of the radiation treatment is to necrose a tumor or suppress growth of the tumor by concentrating high dose radiation on the tumor while minimizing the disorder of normal surrounding organs.

Since a recently introduced brachytherapy can be performed alone or in combination with an external radiation treatment that irradiates high dose radiation from the outside of a patient and can directly irradiate the high dose radiation onto the tumor, the brachytherapy is widely known as a standard radiation therapy for a cervical cancer that is a female's representative disease. The brachytherapy is one of three-dimensional conformal radiation therapy that uses the effect that very high dose is irradiated onto a region adjacent to a source of the injected isotope but the dose rapidly decreases as a distance from the source increases on the basis of an inverse square law. Therefore, for the success of the brachytherapy, it is important to effectively arrange radiation sources in the proximity of a tumor to be treated.

However, in the past, it was common to perform the brachytherapy by inserting a stereotyped or uniform cylindrical applicator into a patient's body or attaching a sheet-shaped applicator to a patient's body surface.

However, in the case of using such a conventional applicator, a standard applicator has been used which has a uniform applicator shape without taking into consideration physical influence, such as a shape of a tumor, a body type, or a distribution of normal surrounding organs, which is different for each patient receiving a brachytherapy, and has an applicator hole disposed such that a radiation source is fixed thereinside on a predetermined path. Hence, a case where a brachytherapy customized for a patient's actual body type is impossible has inevitably occurred. In particular, since Korea depends entirely on imports for the applicator (about 90% import from the Netherlands), patients of other countries having different body types practically have no choice but to use standard applicators.

The system 1 for manufacturing the patient-specific applicator 32, according to the present embodiment, is a system that designs an applicator structure 16 by using medical images 22 acquired from the medical image analysis device 20 (for example, a magnetic resonance imaging (MRI) apparatus, a computed tomography (CT) apparatus, an ultrasonic apparatus, and the like) and manufactures the patient-specific applicator 32 by using the 3D printing device 30.

Therefore, the use of the system 1 for manufacturing the patient-specific applicator 32 makes it possible to design the patient-specific applicator 32 by using the 3D image having the same condition as the anatomical structure of the patient and manufacture the designed patient-specific applicator 32 by using the 3D printing device. Hence, it is possible to perform an optimized brachytherapy on a tumor tissue according to an actual body type of a patient.

Referring to FIG. 1, the medical image analysis device 20 means a general apparatus that captures medical images 22 of a patient's body and stores and analyzes the captured medical images 22. More specifically, as described above, the medical image analysis device 20 includes commonly known apparatus for acquiring various types of the medical images 22, such as an MRI apparatus, a CT apparatus, an ultrasonic apparatus, and an X-ray apparatus. That is, the medical image analysis device 20 is an apparatus for acquiring the medical images 22 of the patient, such as an MRI image, a CT image, an ultrasonic image, and an X-ray image and analyze the medical images 22. Since the medical image analysis device 20 is obvious to those skilled in the art, a detailed description thereof will be omitted.

The computing device 20 reconstructs the 3D image 12 depicting a patient's actual anatomical structure by using the medical images 22 received from the medical image analysis device 20. The computing device 20 designs (models) the applicator structure 16 by using the reconstructed 3D image 12 and generates printing data for 3D printing with respect to the designed applicator structure 16.

The 3D printing device 30 is an apparatus including a commonly known 3D printer. In particular, the 3D printing device 30 means an apparatus for three-dimensionally prints a desired structure by using one of a method of manufacturing a structure while stacking plastic or a photocurable material according to the received printing data and a method of manufacturing a structure by carving plastic or a photocurable material according to the received printing data.

The 3D printing device 30 according to the present embodiment manufactures the patient-specific applicator 32 based on the printing data for the 3D printing which is generated by the computing device 20.

As such, since the applicator structure 16 designed by the computing device 20 is obtained by the design (modeling) using the medical images 22 of the patient, the patient-specific applicator 32 manufactured by the 3D printing device 30 may be used for performing a customized brachytherapy capable of accurately treating only a tumor tissue, without influence of radiation treatment on normal tissues, while matching the position or shape of the tumor appearing in the patient's actual body type or actual anatomical structure.

In the following, the operation and function of the computing device 1 for generating printing data for 3D printing before the patient-specific applicator 32 is printed will be described in more detail.

Figure 2:
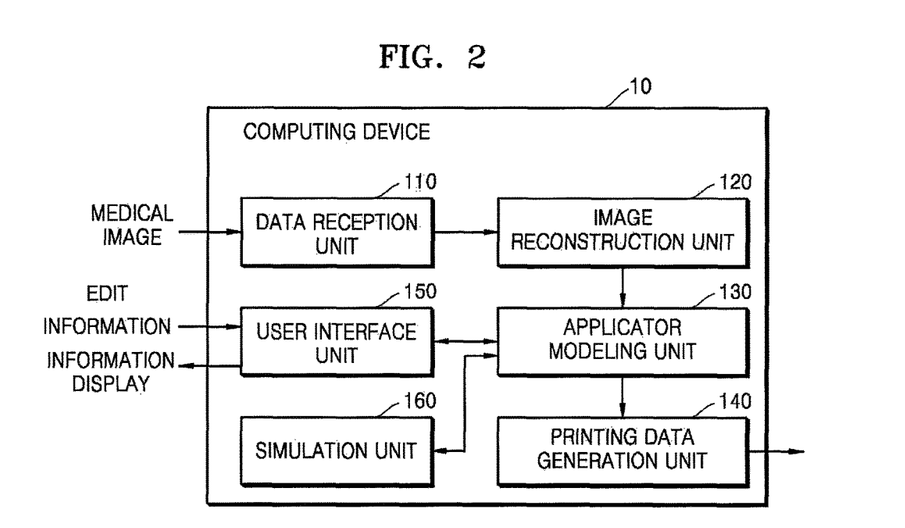
FIG. 2 is a detailed configuration diagram of a computing device in a system for manufacturing a patient-specific applicator, according to an embodiment of the present invention.

FIG. 2 is a detailed configuration diagram of the computing device 10 in the system 1 for manufacturing the patient-specific applicator 32, according to the embodiment of the present invention.

Referring to FIG. 2, the computing device 10 may include a data reception unit 110, an image reconstruction unit 120, an applicator modeling unit 130, a printing data generation unit 140, a user interface unit 150, and a simulation unit 160. On the other hand, in the computing device 100 illustrated in FIG. 2, only elements related to the present embodiment are illustrated so as to prevent the features of the present embodiment from being obscured, but it can be understood by those skilled in the art that general-purpose elements other than the elements illustrated in FIG. 2 may be further included.

Herein, some elements of the computing device 10 may be implemented by at least one commonly used processor. In particular, the image reconstruction unit 120, the applicator modeling unit 130, the printing data generation unit 140, and the simulation unit 160 of the computing device 10 may be implemented by at least one commonly used processor.

The data reception unit 110 receives the medical images (22 of FIG. 1) including the anatomical structure of the patient's body. On the other hand, the medical images (22 of FIG. 1) may store information about the shape, position, and range of the tumor that the patient suffers from, as well as the anatomical structure of the patient's body.

The medical images 22 are data received from the above-described medical image analysis device (20 of FIG. 1) and include an MRI image, a CT image, and an ultrasonic image including information about the anatomical structure of the patient's body or the tumor. Alternatively, the data reception unit 110 may acquire the medical images (22 of FIG. 1) stored in a storage unit (not illustrated) provided inside the computing device 10.

Figure 3:
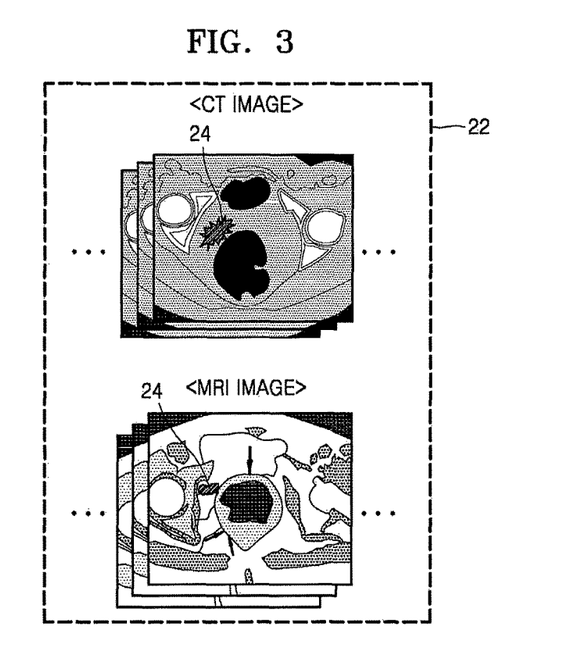
FIG. 3 is a diagram illustrating medical images including information about an anatomical structure of a patient's body or a tumor tissue, according to an embodiment of the present invention.

FIG. 3 is a diagram illustrating the medical images 22 including the information about the anatomical structure of the patient's body or the tumor tissue, according to an embodiment of the present invention. Referring to FIG. 2, the medical images 22 may correspond to a plurality of 2D CT images or a plurality of 2D MRI images acquired by capturing cross-sections of the patient's body. In addition, although not illustrated in FIG. 3, the medical images 22 received from the medical image analysis device 20 may correspond to 3D CT images or 3D MRI images.

Generally, in the medical images 22 such as the CT images or the MRI images, the contour and the anatomical structure of the patient's body are discriminately displayed with different pixel values. The use of these pixel values makes it possible to discriminate anatomical information such as bones and organs of the patient's body.

In addition, the medical images 22 may include information about a tumor tissue 24 of the patient's body, and information about a current shape, distribution, and position of the tumor of the patient's body through the medical images 22.

Referring to FIG. 2 again, the image reconstruction unit 120 reconstructs the 3D image (12 of FIG. 1) depicting the anatomical structure of the patient's body by using the medical images 22 acquired from the patient. At this time, the image reconstruction unit 120 may three-dimensionally reconstruct the internal and external structures of the patient's body by segmenting the anatomical information included in the medical images 22.

In the above-described example of FIG. 3, the medical images 22, such as the plurality of CT images or the plurality of MRI images, correspond to images related to the cross-sections of the patient's body, and the image reconstruction unit 120 three-dimensionally reconstructs the internal and external structures of the patient's body by matching these respective images. Since the process of reconstructing or modeling the 3D image by using the plurality of CT images or the plurality of MRI images is obvious to those skilled in the art, a detailed description thereof will be omitted.

The applicator modeling unit 130 models the applicator structure 16 based on the anatomical structure depicted in the 3D image 12 reconstructed by the image reconstruction unit 120, the applicator structure 16 being to be inserted into the patient's body so as to irradiate radiation onto the tumor tissue (24 of FIG. 3) included in the medical images 22.

More specifically, the applicator modeling unit 130 generates a basic 3D model 14 of the applicator on the 3D images 12, taking into consideration the anatomical structure of the 3D images 12. Then, when a user of the computing device 10 inputs edit information, for example, by increasing or decreasing a length of the basic 3D model 14, or rotating a direction of the basic 3D model 14, or adjusting a refraction angle of the basic 3D model 14 through the user interface unit 150, the applicator modeling unit 130 models the applicator structure 16 by reflecting user's edit information to the basic 3D model 14 and generating a modified 3D model of the applicator.

Alternatively, the applicator modeling unit 130 may model the applicator structure 16 by loading a 3D model matching a position, into which the applicator is to be inserted, on the 3D image 12 from a library related to various 3D models of the applicator which is prestored in the storage unit (not illustrated).

That is, as long as the applicator modeling unit 130 can model the applicator structure 16 matching the position, into which the applicator is to be inserted, on the 3D image 12 of the patient, various methods, such as the edit by the user or the readout from the library, can be used and the present invention is not limited to any one of the methods.

Figure 4A:
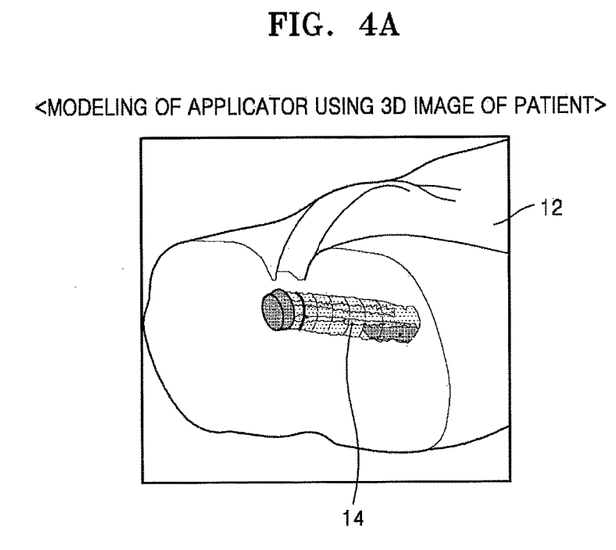
FIG. 4a is a diagram illustrating a process of modeling an applicator by using a 3D image of a patient, according to an embodiment of the present invention.

FIG. 4a is a diagram illustrating a process of modeling the applicator by using the 3D image of the patient, according to an embodiment of the present invention.

Referring to FIG. 4a, the 3D image 12 of the patient is an image that is reconstructed by the image reconstruction unit 120 so as to depict the patient's actual anatomical structure by using the medical images 22 of the patient. As such, since the 3D image 12 is an image reconstructed based on the medical images 22 of the patient, the patient's actual body type or actual anatomical structure can be substantially equally reflected.

The applicator modeling unit 130 models the applicator so as to match a space, into which the applicator is to be inserted, on the 3D image 12 of the patient. For example, when the applicator according to the present embodiment is used for treating a cervical cancer, an insertion passage of a space inside a patient's vagina may be depicted with intaglio on the 3D image 12, and the applicator modeling unit 130 may model the applicator so as to match the insertion passage.

That is, as described above, the applicator modeling unit 130 may model the applicator by generating the basic 3D model 14 of the applicator on the 3D image 12, taking into consideration the anatomical structure of the 3D image 12, and reflecting the user's edit information with respect to the basic 3D model 14, or may model the applicator from the library prestored in the storage unit (not illustrated).

Referring to FIG. 2 again, the applicator modeling unit 130 models the internal structure of the applicator by modeling a passage of an applicator hole, into which a radiation source subjected to short-distance radiation irradiation onto the tumor tissue 24 is inserted, based on the position of the tumor tissue (24 of FIG. 3) appearing on the reconstructed 3D image 12. Such an applicator hole corresponds to a space, into which an isotope corresponding to the radiation source is inserted, in the inside of the applicator.

The applicator hole may be curved according to the shape and position of the tumor tissue 24. In addition, the structure of the applicator hole, such as thickness, length, or traveling direction, may be different according to the shape and position of the tumor tissue 24.

The user may edit the structure of the applicator hole through the user interface unit 150, and the applicator modeling unit 130 may model the structure of the applicator hole inside the applicator by reflecting the user's edit information input through the user interface unit 150. In addition, as in the 3D model (14 of FIG. 1) of the applicator, the structure of the applicator hole may be stored in the storage unit (not illustrated) in a library form, and the applicator modeling unit 130 may model the structure of the applicator hole by using the library.

On the other hand, when the radiation source is inserted into the applicator hole, the applicator modeling unit 130 models an internal material of the applicator surrounding the applicator hole such that the short-distance radiation irradiation is performed on the tumor tissue. In particular, when the radiation source is inserted into the applicator hole, the applicator modeling unit 130 may partially differently model a density or a component of the internal material such that the short-distance radiation irradiation is performed on only the tumor tissue, while shielding the short-distance radiation irradiation on normal tissues.

That is, the applicator modeling unit 130 may partially differently model the material of the applicator so as to match the position and shape of the tumor tissue 24. In addition, the applicator modeling unit 130 may model the material of the applicator into a material that the user inputs through the user interface unit 150.

The user may previously measure a transmission strength of the radiation with respect to materials having various densities, prestore the measured transmission strength of the radiation in the computing device 10 in a library form, select one or more of them, and directly model the material of the applicator. Therefore, the applicator modeling unit 130 may model the entire applicator with the same material or may individually model a portion desired by the user or a portion near the tumor with different materials. For example, when a material of a specific portion of the applicator with a heavy metal, a partial shielding design of the radiation is possible.

On the other hand, the applicator modeling unit 130 may simply and smoothly model the surface of the 3D model 14 of the applicator such that the patient-specific applicator (32 of FIG. 1) to be manufactured can be easily inserted into the patient's body.

Furthermore, the applicator modeling unit 130 may further model a joining means that is connectable to one end of the applicator and guides a connection to an external treatment device or a fixing device.

Figure 4B:
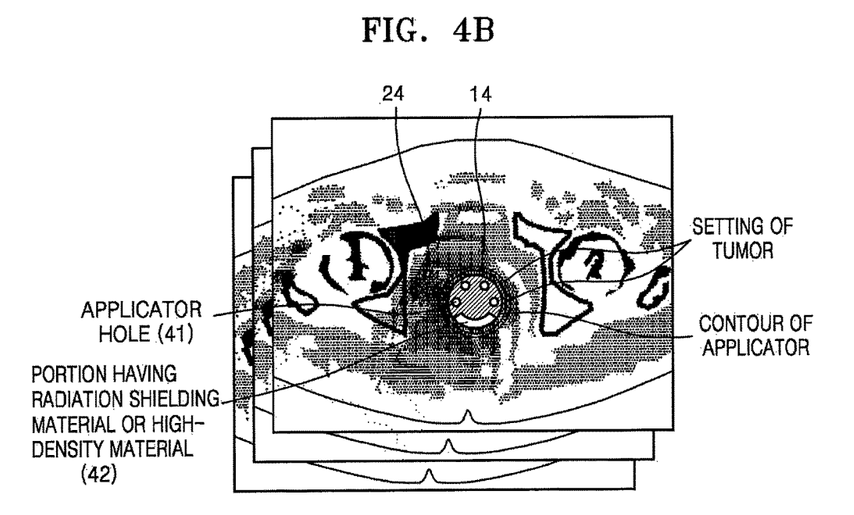
FIG. 4b is a diagram illustrating a process of modeling an applicator by using a 3D image of a patient, according to an embodiment of the present invention.

FIG. 4b is a diagram illustrating a process of modeling the applicator by using the 3D image of the patient, according to an embodiment of the present invention.

Referring to FIG. 4b, as described above, the applicator modeling unit 130 may model at least one applicator hole 41 in the inside of the 3D model 14 of the applicator. In addition, the applicator modeling unit 130 may partially model a material capable of shielding the radiation in the inside of the 3D model 14 of the applicator such that the short-distance radiation irradiation is shielded on the normal tissues and the short-distance radiation irradiation is performed on only the tumor tissue.

Referring to FIG. 2 again, the applicator modeling unit 130 may model the external structure of the applicator by displaying a mark for indicating an insertion degree of the applicator in the inside of the patient's body on the surface of the applicator. In addition, the applicator modeling unit 130 may model the external structure of the applicator so as to display a mark for identification information (name, ID, etc.) for identification of the patient, an insertion direction, and the like. These marks may be carved on the surface in a fine groove form when the applicator is actually manufactured.

Then, the printing data generation unit 140 generates printing data for 3D printing for manufacturing the patient-specific applicator 32, based on the applicator structure 16 modeled by the applicator modeling unit 130. The printing data is data having a format required for printing the 3D structure in the 3D printing device (30 of FIG. 1). That is, the printing data generation unit 140 converts image data of the applicator structure 16 into printing data having a format that can be by the 3D printing device 30. Since the printing data having the converted format is obvious to those skilled in the art in the technical field related to the 3D printing device 30, a detailed description will be omitted.

The 3D printing device 30 receives the printing data for the 3D printing which is generated by the printing data generation unit 140, and manufactures the patient-specific applicator 32 based on the printing data for the 3D printing.

Figure 5:
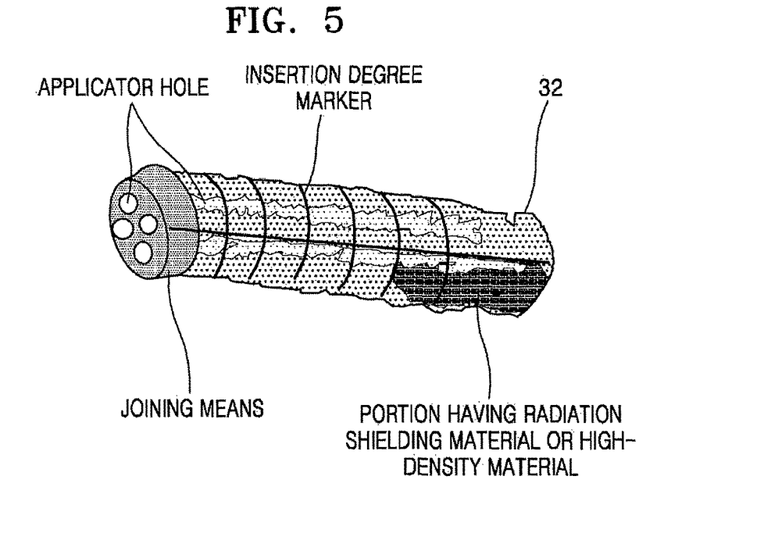
FIG. 5 is a diagram illustrating a patient-specific applicator manufactured by a 3D printing device, according to an embodiment of the present invention.

FIG. 5 is a diagram illustrating the patient-specific applicator 32 manufactured by the 3D printing device 30, according to the embodiment of the present invention. The patient-specific applicator 32 manufactured by the 3D printing device 30 is a structure that is manufactured by stacking plastic or a photocurable material in the 3D printing device (30 of FIG. 1) or a structure that is manufactured by carving plastic or a photocurable material.

A mark is displayed on the surface of the patient applicator 32 so as to indicate the insertion degree of the applicator 32 with respect to the patient's body. The patient applicator 32 is manufactured in a shape in which a passage of at least one applicator hole is empty. On the other hand, a joining means that guides a connection to an external treatment device or a fixing device is connected to an inlet of the applicator hole or one end of the patient applicator 32. Furthermore, the inside of the patient applicator 32 is manufactured by partially using a material that can shield the radiation so as to shield the short-distance radiation irradiation onto the normal tissues.

As described above, since the patient-specific applicator 32 is manufactured after the design (modeling) based on the patient's medical images 22 in the computing device 20, the patient-specific applicator 32 can perform a customized brachytherapy capable of accurately treating only a tumor tissue, without influence of radiation treatment on the normal tissues, while matching the position or shape of the tumor appearing in the patient's actual body type or actual anatomic structure. In addition, since the patient-specific applicator 32 is manufactured by using the 3D printing device 30, the applicator suitable for the patient's actual body type can be manufactured more easily and at a low cost.

Referring to FIG. 2 again, the computing device 10 may further include a simulation unit 160 that performs simulation on the modeled applicator structure 16 so as to manufacture the patient-specific applicator more accurately.

Figure 6:
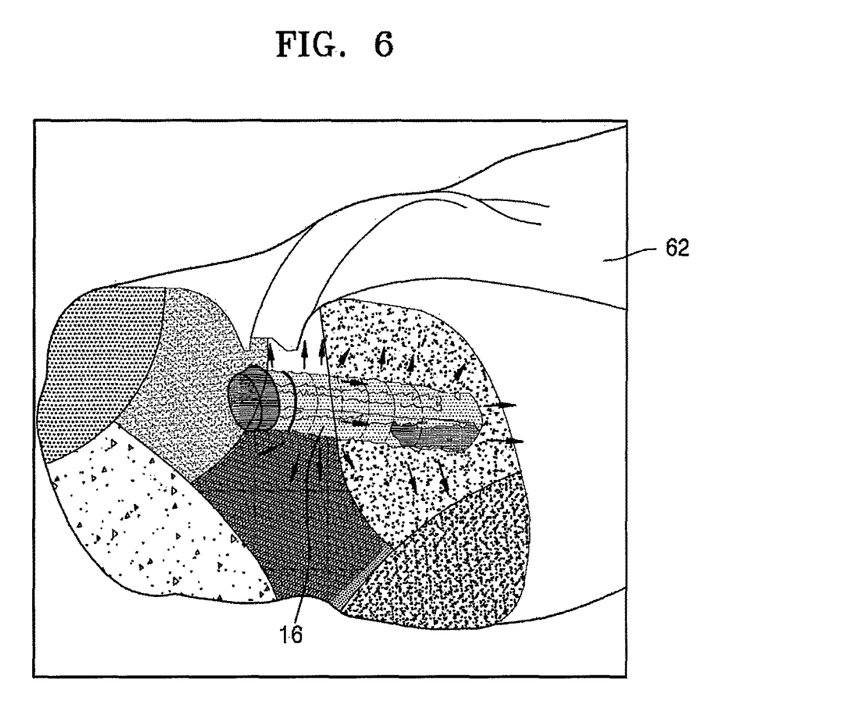
FIG. 6 is a diagram illustrating a process of performing simulation on a modeled applicator structure in a simulation unit, according to an embodiment of the present invention.

FIG. 6 is a diagram illustrating a process of performing simulation on the modeled applicator structure 16 in the simulation unit 160, according to an embodiment of the present invention.

Before the simulation unit 160 performs the simulation, the image reconstruction unit 120 reconstructs a 3D density image 62 depicting density distributions of internal constituent materials of the patient's body by using pixel values of the medical images 22 acquired from the patient. As such, the 3D density image 62 corresponds to a patient's virtual body and is an image corresponding to the density distributions of the internal constituent materials of the patient's body. Herein, since the densities corresponding to the respective pixels of the medical images 22 are converted into relative densities based on the density of water, the 3D density image 62 may be configured with pixels having converted relative density values.

The simulation unit 160 places the modeled applicator structure 16 at the insertion position of the actual applicator in the reconstructed 3D density image 62. The simulation unit 160 simulates a change in the patient's body, in a case where the applicator is inserted, by using a change in the pixel values of the 3D density image 62 at the position of the applicator structure 16.

More specifically, the simulation unit 160 moves the respective pixels of the 3D density image 62 overlapped at the position of the applicator structure 16 to the outside of the applicator structure 16. At this time, the simulation unit 160 calculates a resistance according to a movement of each pixel with respect to a relative density based on water. Since the resistance according to the movement of each pixel increases as the relative density becomes higher, the simulation unit 160 may assign a lower moving weight to each pixel. In addition, the simulation unit 160 may assign a higher moving weight to a pixel nearer from the end of the applicator structure 16, as compared with a pixel farther away from the end of the applicator structure 16 By expressing the moving flow of the pixels in an optic flow form, the simulation unit 160 may provide an image corresponding to a simulation result so that the user can know a change in the patient's body through the user interface unit 150 when the applicator is inserted. In addition, the simulation unit 160 may provide an image corresponding to the simulation result by mapping information of each pixel modified by the 3D density image 62 again to the pixel values of the medical images 22.

In a case where such a simulation process is undergone, the printing data generation unit 140 may generate printing data only when it is determined through the simulation result that there is no problems in the applicator or the patient.

Figure 7:
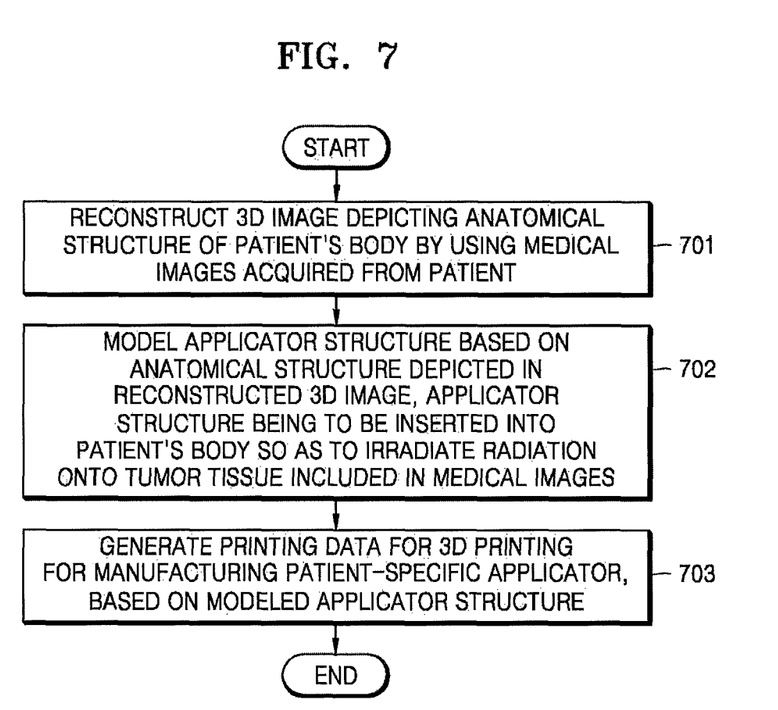
FIG. 7 is a flowchart of a method for manufacturing a patient-specific applicator, according to an embodiment of the present invention.

FIG. 7 is a flowchart of a method for manufacturing a patient-specific applicator 32, according to an embodiment of the present invention. Referring to FIG. 7, the method for manufacturing the patient-specific applicator 32 is processes that are performed in time series by the system 1 of FIG. 1 for manufacturing the patient-specific applicator. Therefore, even though omitted in the following, the contents described above can also be applied to the method of FIG. 7 for manufacturing the patient-specific applicator 32.

In step 701, the image reconstruction unit 120 reconstructs the 3D image 12 depicting the anatomical structure of the patient's body by using the medical images 22 acquired from the patient.

In step 702, the applicator modeling unit 130 models the applicator structure 16 based on the anatomical structure depicted in the reconstructed 3D image 12, the applicator structure 16 being to be inserted into the patient's body so as to irradiate radiation onto the tumor tissue 24 included in the acquired medical images 22.

In step 703, the printing data generation unit 130 generates printing data for 3D printing for manufacturing the patient-specific applicator 32, based on the modeled applicator structure 16.

The above-described embodiments of the present invention can be embodied as computer programs and can be implemented in general-purpose digital computers that execute the programs using a computer-readable recording medium. In addition, the structures of data used in the above-described embodiments of the present invention can be recorded in computer-readable recording medium through a variety of means. Examples of the computer-readable recording medium include magnetic storage media (e.g., ROM, floppy disks, hard disks, etc.) and optical readable media (e.g., CD-ROMs, or DVDs).

While this invention has been particularly shown and described with reference to preferred embodiments thereof, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. An apparatus for generating printing data for a patient-specific applicator, the apparatus comprising:
    an image reconstruction unit to reconstruct a three-dimensional (3D) image depicting an anatomical structure of a patient's body by using a medical image acquired from the patient;
    an applicator modeling unit to model an applicator structure based on the anatomical structure depicted in the reconstructed 3D image, the applicator structure is inserted into the patient's body so as to irradiate radiation onto a tumor tissue included in the acquired medical image; and
    a printing data generation unit to generate printing data for 3D printing for manufacturing the patient-specific applicator, based on the modeled applicator structure,
    wherein the applicator modeling unit models an internal structure of the applicator by modeling a passage of an applicator hole, into which a radiation source subjected to short-distance radiation irradiation onto the tumor tissue is inserted, based on a position of the tumor tissue appearing on the reconstructed 3D image.

2. The apparatus of claim 1, wherein the applicator modeling unit models an internal material of the applicator surrounding the applicator hole such that the short-distance radiation irradiation is performed on the tumor tissue when the radiation source is inserted into the applicator hole.

3. The apparatus of claim 2, wherein, when the radiation source is inserted into the applicator hole, the applicator modeling unit partially differently models a density or a component of the internal material so as to shield short-distance radiation irradiation on normal tissues.

4. The apparatus of claim 1, wherein the applicator modeling unit models an external structure of the applicator by displaying a mark for indicating an insertion degree of the applicator in the inside of the patient's body on a surface of the applicator.

5. The apparatus of claim 1, wherein the applicator modeling unit further models a joining means that is connectable to one end of the applicator and guides a connection to an external treatment device or a fixing device.

6. The apparatus of claim 1, wherein the image reconstruction unit reconstructs a 3D density image depicting density distributions of internal constituent materials of the patient's body by using pixel values of the medical image acquired from the patient,
the apparatus further comprises a simulation unit to simulate a change in the patient's body, in a case where the applicator is inserted, by using a change in pixel values of positions at which the modeled applicator structure is to be inserted in the reconstructed 3D density image, and
the printing data generation unit to generate the printing data when it is determined through a simulation result that there is no problems in the applicator or the patient.

7. A method for generating printing data for a patient-specific applicator, the method comprising the steps of:
reconstructing a three-dimensional (3D) image depicting an anatomical structure of a patient's body by using a medical image acquired from the patient;
modeling an applicator structure based on the anatomical structure depicted in the reconstructed 3D image, the applicator structure is inserted into the patient's body so as to irradiate radiation onto a tumor tissue included in the acquired medical image; and
generating printing data for 3D printing for manufacturing the patient-specific applicator, based on the modeled applicator structure,
wherein the modeling step models an internal structure of the applicator by modeling a passage of an applicator hole into which a radiation source subjected to short-distance radiation irradiation onto the tumor tissue is inserted, based on a position of the tumor tissue appearing on the reconstructed 3D image.

8. The method of claim 7, wherein the modeling step models an internal material of the applicator surrounding the applicator hole such that the short-distance radiation irradiation is performed on the tumor tissue when the radiation source is inserted into the applicator hole.

9. The method of claim 7, wherein the modeling step models an external structure of the applicator by displaying a mark for indicating an insertion degree of the applicator in the inside of the patient's body on a surface of the applicator.

10. The method of claim 7, further comprising the step of modeling a joining means that is connectable to one end of the modeled applicator structure and guides a connection to an external treatment device or a fixing device,
wherein the generating step generates the printing data based on the modeled applicator structure and the joining means.

11. The method of claim 7, further comprising the steps of:
reconstructing a 3D density image depicting density distributions of internal constituent materials of the patient's body by using pixel values of the medical image acquired from the patient; and
simulating a change in the patient's body, in a case where the applicator is inserted, by using a change in pixel values of positions at which the modeled applicator structure is to be inserted in the reconstructed 3D density image,
wherein the generating step generates the printing data when it is determined through a simulation result that there is no problems in the applicator or the patient.

12. A system for manufacturing a patient-specific applicator, the system comprising:
a computing device to reconstruct a three-dimensional (3D) image depicting an anatomical structure of a patient's body by using a medical image acquired from the patient, models an applicator structure based on the anatomical structure depicted in the reconstructed 3D image, the applicator structure is inserted into the patient's body so as to irradiate radiation onto a tumor tissue included in the acquired medical image, and generates printing data for 3D printing for manufacturing the patient-specific applicator, based on the modeled applicator structure; and
a 3D printing device to manufacture the patient-specific applicator based on the generated printing data,
wherein the computing device models an internal structure of the applicator by modeling a passage of an applicator hole, into which a radiation source subjected to short-distance radiation irradiation onto the tumor tissue is inserted, based on a position of the tumor tissue appearing on the reconstructed 3D image.

13. The system of claim 12, wherein the computing device models an internal structure of the applicator by modeling a passage of an applicator hole, into which a radiation source subjected to short-distance radiation irradiation onto the tumor tissue is inserted, based on a position of the tumor tissue appearing on the reconstructed 3D image.

14. The system of claim 13, wherein the computing device models an internal material of the applicator surrounding the applicator hole such that the short-distance radiation irradiation is performed on the tumor tissue when the radiation source is inserted into the applicator hole.

* * * * *